United States Patent [19]

Heitsch et al.

[11] Patent Number: 5,236,943
[45] Date of Patent: Aug. 17, 1993

[54] METHOD FOR THE TREATMENT OF CARDIAC AND OF VASCULAR HYPERTROPHY AND HYPERPLASIA

[75] Inventors: Holger Heitsch, Hofheim am Taunus; Rainer Henning, Hattersheim am Main; Wolfgang Linz, Mainz; Bernward Schölkens, Kelkheim/Taunus; Hansjörg Urbach, Kronberg/Taunus, all of Fed. Rep. of Germany

[73] Assignee: Hoechst Aktiengesellschaft, Frankfurt am Main, Fed. Rep. of Germany

[21] Appl. No.: 791,501

[22] Filed: Nov. 14, 1991

[30] Foreign Application Priority Data

Nov. 17, 1990 [DE] Fed. Rep. of Germany ....... 4036706

[51] Int. Cl.[5] ................ A61K 31/415; A61K 31/535; A61K 31/41
[52] U.S. Cl. .................................. 514/397; 514/396; 514/231.2; 514/231.5; 514/381
[58] Field of Search .................. 514/397, 235.5, 235, 514/374, 322, 381, 394, 231.2, 231.5, 396, 381

[56] References Cited

U.S. PATENT DOCUMENTS

| | | | |
|---|---|---|---|
| 4,355,040 | 10/1982 | Furukawa et al. | 424/273 R |
| 4,880,804 | 11/1989 | Carini et al. | 514/234.5 |
| 4,916,129 | 4/1990 | Carini et al. | 514/235.2 |
| 4,975,444 | 12/1990 | Danilewicz et al. | 514/354 |

FOREIGN PATENT DOCUMENTS

| | | |
|---|---|---|
| 0028833 | 5/1981 | European Pat. Off. . |
| 0028834 | 5/1981 | European Pat. Off. . |
| 0291969 | 11/1988 | European Pat. Off. . |
| 0323841 | 7/1989 | European Pat. Off. . |
| 0324377 | 7/1989 | European Pat. Off. . |

OTHER PUBLICATIONS

"The Discovery of Potent Nonpeptide Angiotensin II Receptor Antagonists: A New Class of Potent Antihypertensives" by J. V. Duncia et al., J. Med. Chem. (1990) vol. 33, pp. 1312–1329.
"Nonpeptide Angiotensin II Receptor Antagonists. IV. EXP6155 and EXP6803" by P. C. Wong et al., Hypertension vol. 13, No. 5 (1989) pp. 489–497.
"Nonpeptide Angiotensin II (AII) Receptor Antagonists: Studies With EXP9270" by P. C. Wong et al., Hypertensio vol. 14, No. 3 (1989) p. 348.
"Hypotensive Action of DuP 753, an Angiotensin II Antagonist, in Spontaneously Hypertensive Rats" by P. C. Wong et al., Hypertension vol. 15, No. 5 (1990) pp. 459–468.
"EXP 6803, A Nonpeptide Angiotensin II Receptor Antagonist" by P. C. Wong et al., Cardiovascular Drug Reviews vol. 7, No. 4 (1989) pp. 285–300.
"Two Distinct Angiotensin II Receptor Binding Sites in Rat Adrenal Revealed by New Selective Nonpeptide Ligands" by R. S. L. Chang et al., Molecular Pharmacology vol. 29 (1990) pp. 347–351.
"Antihypertensive Mechanism of Captopril in Renal Hypertensive Rats: Studies with a Nonpeptide Angiotensin II Receptor Antagonist and an Angiotensin II Monoclonal Antibody" by P. C. Wong et al., The Journal of Pharmacology and Experimental Therapeutics, vol. 250, No. 2 (1989) pp. 515–522.
"Nonpeptide Angiotensin II Receptor Antagonists. III. Structure-Function Studies[1]" by A. T. Chiu et al., The Journal of Pharmacology and Experimental Therapeutics, vol. 250, No. 3 (1989) pp. 867–874.
"Nonpeptide Angiotensin II Receptor Antagonists. VII.[1] Cellular and Biochemical Pharmacology of DuP 753, an Orally Active Antihypertensive Agent" by P. C. Wong et al., The Journal of Pharmacology and Experimental Therapeutics, vol. 252, No. 2 (1990) pp. 711–718.
"Nonpeptide Angiotensin II Receptor Antagonists. VIII.[1] Characterization of Functional Antagonism Displayed by DuP 753, and Orally Active Antihypertensive Agent" by P. C. Wong et al., The Journal of Pharmacology and Experimental Therapeutics vol. 252, No. 2 (1990) pp. 719–725.
"Nonpeptide Angiotensin II Receptor Antagonists. IX.[1] Antihypertensive Activity in Rats of DuP 753, and Orally Active Antihypertensive Agent" by P. C. Wong et al., The Fournal of Pharmacology and Experimental Therapeutics vol. 252, No. 2 (1990) pp. 726–732.
Devereux et al., J. Clin Hypertens 1987: 3:87–103.
Dzau et al., Hypertension, vol. 18, No. 4, Oct. 1991, pII–100–104.
Sachinidis et al., Journal of Hypertension 1991, 9 (suppl 6):S226–S227.
Linz et al., Journal of Hypertension 1991, 9 (suppl 6):S400–S401.

*Primary Examiner*—Frederick E. Waddell
*Assistant Examiner*—T. J. Criares
*Attorney, Agent, or Firm*—Finnegan, Henderson, Farabow, Garrett & Dunner

[57] ABSTRACT

The invention relates to a method for the treatment of cardiac and of vascular hypertrophy and/or hyperplasia by administration of angiotensin II receptor blockers, preferably of the imidazole, pyrrole, pyrazole, triazole or tetrazole type.

5 Claims, No Drawings

METHOD FOR THE TREATMENT OF CARDIAC AND OF VASCULAR HYPERTROPHY AND HYPERPLASIA

The invention relates to a method for the treatment of cardiac and of vascular hypertropyhy and/or hyperplasia by use of compounds which block the angiotensin II receptor.

The invention also relates to the use of angiotensin II receptor blockers for the preparation of medicaments for the treatment of cardiac as well as of vascular hypertrophy and/or hyperplasia.

Substituted imidazoles, pyrroles, pyrazoles and triazoles are known as antihypertensives and agents for the treatment of cardiac insufficiency from EP-A 028,833, EP-A 028,834, EP-A 323,841, EP-A 324,377, EP-A 291,969, US-A 4,355,040, US-A 4,880,804 and US-A 4,916,129 and from J. Med. Chem., Vol. 33, 1312 (1990); Hypertension, Vol. 13, 489 (1989); Hypertension, Vol. 14, 348 (1989); Hypertension, Vol. 15, 459 (1990); Cardiov. Drug Rev., Vol. 7, 285 (1989); Mol. Pharmacol., Vol. 37, 347 (1990); J. Pharmacol. Exp. Ther., Vol. 250, 515 (1989); J. Pharmacol. Exp. Ther., Vol. 250, 867 (1989); J. Pharmacol. Exp. Ther., Vol. 252, 711 (1990); J. Pharmacol. Exp. Ther., Vol. 252, 719 (1990) and J. Pharmacol. Exp. Ther., Vol. 252, 726 (1990).

It has now surprisingly been found that compounds of these structure types additionally are highly active and highly specific cardioprotectives which are able to abolish hypertrophy and hyperplasia of smooth vascular muscle and of cardiac muscle.

Suitable compounds of the formula I

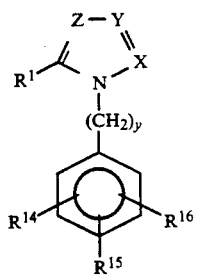

(I)

are in this case particularly those in which a) X, Y and Z are identical or different and are N or $CR^2$, b) $R^1$ is
1. $(C_2-C_{10})$-alkyl,
2. $(C_3-C_{10})$-alkenyl,
3. $(C_3-C_{10})$-alkynyl,
4. $OR^3$,
5. $(C_3-C_8)$-cycloalkyl,
6. $(C_4-C_{10})$-cycloalkylalkyl,
7. $(C_5-C_{10})$-cycloalkylalkenyl,
8. $(C_5-C_{10})$-cycloalkylalkynyl,
9. $-(CH_2)_m-B-(CH_2)_n-R^4$,
10. benzyl,
11. a radical as defined under b) 1., 2., 3. or 9., which is monosubstituted by $CO_2R^3$,
12. a radical as defined under b) 1., 2., 3. or 9., in which 1 to all of the hydrogen atoms are substituted by fluorine, or
13. the radical defined under b) 10., which is substituted on the phenyl by 1 to 2 identical or different radicals from the series comprising halogen, $(C_1-C_4)$-alkoxy and nitro;

c) $R^2$ is
1. hydrogen,
2. halogen,
3. nitro,
4. $C_\nu F_{2\nu+1}$,
5. $SF_5$,
6. pentafluorophenyl,
7. cyano,
8. phenyl,
9. phenyl-$(c_1-C_3)$-alkyl,
10. $(C_1-C_{10})$-alkyl,
11. $(C_3-C_{10})$-alkenyl,
12. phenyl-$(C_2-C_6)$-alkenyl,
13. 1-imidazolyl—$(CH_2)_m$—,
14. 1,2,3-traizolyl—$(CH_2)_n$—,
15. tetrazolyl—$(CH_2)_m$—,
16. $-(CH_2)_{o-1}-CHR^7-OR^5$,
17. $-(CH_2)_o-O-CO-R^3$,
18. $-(CH_2)_o-S-R^6$,
19. $-S(O)_r-R^6$,
20. $-CH=CH-(CH_2)_m-CHR^3-OR^6$,
21. $-CH_2=CH-(CH_2)_m-CO-R^8$,
22. $-CO-R^8$,
23. $-CH=CH-(CH_2)_m-O-CO-R^7$,
24. $-(CH_2)_m-CH(CH_3)-CO-R^8$,
25. $-(CH_2)_o-CO-R^8$, 26. $-(CH_2)_o-O-\underset{\underset{W}{\|}}{C}-NH-R^9$, 27. $-(CH_2)_o-NR^7-\underset{\underset{W}{\|}}{C}-OR^9$, 28. $-(CH_2)_o-NR^7-CO-NHR^9$,
29. $-(CH_2)_o-NR^7-SO_2R^9$, 30. $-(CH_2)_o-NR^7-\underset{\underset{W}{\|}}{C}-R^9$, 31. $-(CH_2)_nF$,
32. $-(CH_2)_n-O-NO_2$,
33. $-CH_2-N_3$,
34. $-(CH_2)_n-NO_2$,
35. $-CH=N-NR^5R^7$,
36. phthalimido—$(CH_2)_n$—, 37. $-(CH_2)_n-\underset{R^{10}}{\overset{N=N}{\diagup\!\!\!\diagdown}}NH$ 38. $-(CH_2)_n-\underset{\underset{H}{|}}{\overset{N-N}{\diagup\!\!\!\diagdown}}\underset{N}{\diagdown}CF_3$ 39. $-(CH_2)_n-N\diagdown\diagup N-\underset{OCH_3}{\diagdown}$ 40. 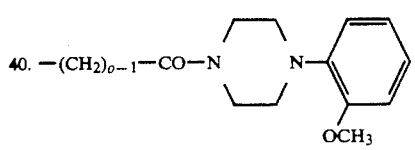

41. phenyl-SO$_2$—NH—N=CH—,

42. 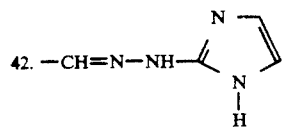

43. —(CH$_2$)$_n$—SO$_2$—NR$^7$—CO—NR$^6$R$^9$,
44. —(CH$_2$)$_o$—SO$_2$R$^9$,
45. a radical as defined under c) 9., 10. or 20., which is substituted on the phenyl by 1 or 2 identical or different radicals from the series comprising halogen, hydroxyl, methoxy, trifluoromethyl, CO$_2$R$^3$ and phenyl,
46. a radical as defined under c) 11. or 12., in which 1 hydrogen atom is substituted by hydroxyl or in which 1 to all of the hydrogen atoms are substituted by fluorine, or
47. the radical defined under c) 15., which is substituted by 1 or 2 identical or different radicals from the series comprising methoxycarbonyl and (C$_1$-C$_4$)-alkyl;

d) R$^3$ is
1. hydrogen,
2. (C$_1$-C$_8$)-alkyl
3. (C$_3$-C$_8$)-cycloalkyl,
4. phenyl,
5. benzyl or
6. the radical defined under d) 2., in which 1 to all of the hydrogen atoms are substituted by fluorine;

e) R$^4$ is
1. hydrogen,
2. (C$_1$-C$_6$)-alkyl,
3. (C$_3$-C$_8$)-cycloalkyl,
4. (C$_2$-C$_4$)-alkenyl or
5. (C$_2$-C$_4$)-alkynyl;

f) R$^5$ is
1. hydrogen,
2. (C$_1$-C$_6$)-alkyl,
3. (C$_3$-C$_8$)-cycloalkyl,
4. phenyl or
5. benzyl;

g) R$^6$ is
1. hydrogen,
2. (C$_1$-C$_6$)-alkyl,
3. (C$_3$-C$_8$)-cycloalkyl,
4. (C$_6$-C$_{12}$)-aryl, preferably phenyl,
5. benzyl,
6. (C$_1$-C$_9$)-heteroaryl which can be partially or completely hydrogenated, preferably 2-pyrimidinyl,
7. (C$_1$-C$_4$)-alkanoyl,
8. a radical as defined under g) 4. or 6., substituted by 1 or 2 identical or different radials from the series comprising halogen, hydroxyl, methoxy, nitro, cyano, CO$_2$R$^3$ and trifluoromethyl, or NR$^{11}$R$^{12}$,
9. (C$_1$-C$_9$)-heteroaryl-(C$_1$-C$_3$)-alkyl, where the heteroaryl moiety can be partially or completely hydrogenated;

h) R$^7$ is
1. hydrogen,
2. (C$_1$-C$_6$)-alkyl,
3. (C$_3$-C$_8$)-cycloalkyl,
4. (C$_6$-C$_{12}$)-aryl-(C$_1$-C$_6$)-alkyl, preferably benzyl,
5. phenyl or
6. (C$_1$-C$_9$)-heteroaryl;

i) R$^8$ is
1. hydrogen,
2. (C$_1$-C$_6$)-alkyl,
3. (C$_3$-C$_8$)-cycloalkyl,
4. phenyl—(CH$_2$)$_q$—,
5. OR$^5$,
6. NR$^{11}$R$^{12}$ or
7. 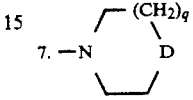

j) R$^9$ is
1. (C$_1$-C$_6$)-alkyl,
2. 1-adamantyl,
3. 1-naphthyl,
4. 1-naphthlethyl,
5. phenyl—(CH$_2$)$_q$— or
6. the radical defined under j) 1., in which 1 to all of the hydrogen atoms are substituted by fluorine;

k) R$^{10}$ is cyano, nitro or CO$_2$R$^7$;
l) R$^{11}$ and R$^{12}$ are identical or different and are
1. hydrogen,
2. (C$_1$-C$_4$)-alkyl,
3. phenyl,
4. benzyl or
5. α-methylbenzyl;

m) D is NR$^{13}$, O or CH$_2$;
n) R$^{13}$ is hydrogen, (C$_1$-C$_4$)-alkyl or phenyl;
o) B is O, NR$^7$ or S;
p) W is O or S;
q) m is an integer from 0 to 5;
r) n is an integer from 1 to 5;
s) o is an integer from 1 to 10;
t) q is 0 or 1;
u) r is 0, 1 or 2, and
v) v is an integer from 1 to 6;
w) R$^{14}$ is 4—CO$_2$H, 4—CO$_2$R$^{18}$,

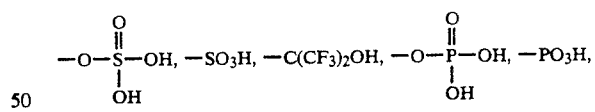

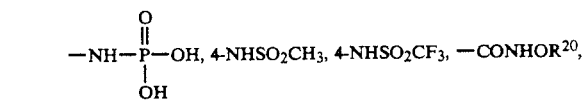

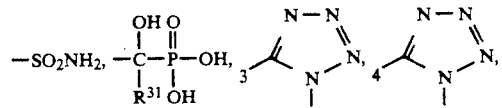

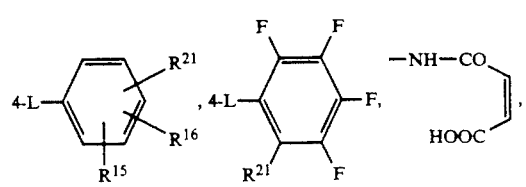

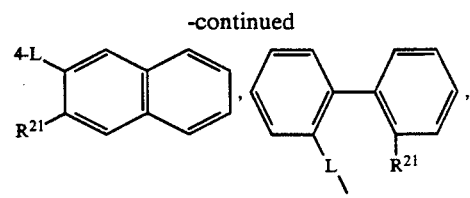

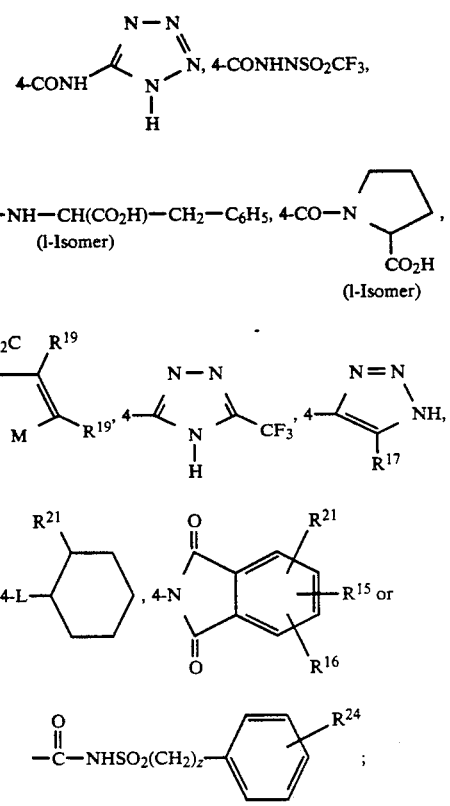

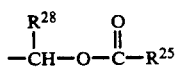

x) $R^{15}$ is hydrogen, halogen, —$NO_2$, —CN, ($C_1$-$C_4$)-alkyl, ($C_1$-$C_4$-acyloxy, ($C_1$-$C_4$)-alkoxy, —$CO_2H$, —$CO_2R^{18}$, —N—$SO_2CH_3$, —$NHSO_2CF_3$, —CONHOR$^{20}$, —$SO_2NH_2$, aryl, furyl or

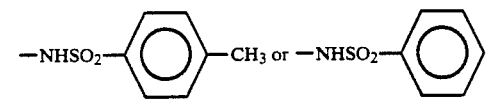

y) $R^{16}$ is hydrogen, halogen, ($C_1$-$C_4$)-alkyl or ($C_1$-$C_4$)-alkoxy;

z) $R^{17}$ is —CN, —$NO_2$ or —$CO_3R^{19}$;

a') $R^{18}$ is the substituent $$-\overset{R^{28}}{\underset{|}{CH}}-O-\overset{O}{\underset{||}{C}}-R^{25}$$

b') $R^{19}$ is hydrogen, ($C_1$-$C_6$)-alkyl, ($C_3$-$C_6$)-cycloalkyl, phenyl or benzyl;

c') $R^{20}$ is hydrogen, methyl or benzyl;

d') $R^{21}$ is

—$CO_2H$, —$CO_2R^{18}$, —$CH_2CO_2H$, —$CH_2CO_2R^{18}$,

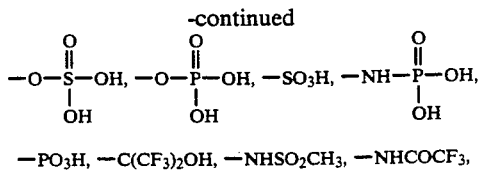

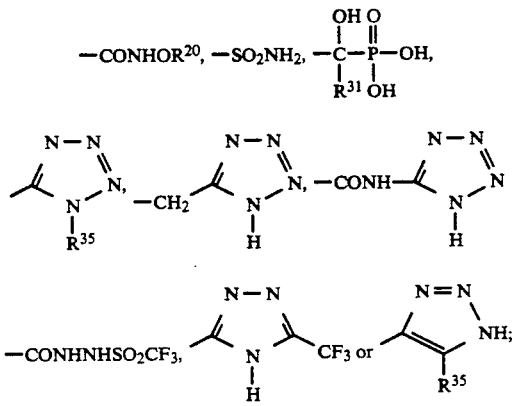

e') $R^{22}$ is hydrogen, ($C_1$-$C_8$)-alkyl or -perfluoroalkyl, ($C_3$-$C_6$)-cycloalkyl, phenyl or benzyl;

f') $R^{23}$ is hydrogen, ($C_1$-$C_6$)-alkyl, ($C_3$-$C_6$)-cycloalkyl, phenyl or benzyl;

g') $R^{24}$ is hydrogen, ($C_1$-$C_4$)-alkyl, ($C_3$-$C_6$)-cycloalkyl, phenyl or benzyl;

h') $R^{25}$ is ($C_1$-$C_6$)-alkyl, —$NR^{26}R^{27}$ or $$NH_2-\overset{|}{C}HCH_2CO_2CH_3;$$

i') $R^{26}$ and $R^{27}$ are identical or different and are hydrogen, ($C_1$-$C_6$)-alkyl or benzyl, or together form a ($CH_2$)$_{n'}$— group where n'=3-6;

j') $R^{28}$ is hydrogen, methyl or phenyl;

k') $R^{29}$ is $NR^{31}R^{32}$, $NHCONH_2$, $NHCSNH_2$,

—NHSO$_2$—⟨phenyl⟩—$CH_3$ or —NHSO$_2$—⟨phenyl⟩ l') $R^{30}$ is hydrogen, ($C_1$-$C_6$)-alkyl, benzyl or alkyl;

m') $R^{31}$ and $R^{32}$ are identical or different and are hydrogen, ($C_1$-$C_5$)-alkyl or phenyl;

n') $R^{33}$ and $R^{34}$ are identical or different and are ($C_1$-$C_4$)-alkyl or together form —($CH_2$)$_x$—;

o') $R^{35}$ is hydrogen, ($C_1$-$C_4$)-alkyl, —$CH_2CH=CH_2$ or —$CH_2C_6H_4R^{36}$;

p') $R^{36}$ is hydrogen, —$NO_2$, —$NH_2$, —OH or —$OCH_3$;

q') L is a C—C single bond or is —CO—, —$CH_2$—, —O—, —S—, —NH—, $$-\underset{R^{30}}{\overset{|}{N}}-, -\underset{R^{27}}{\overset{|}{CON}}-, -\underset{R^{27}}{\overset{|}{NCO}}-, -OCH_2-, -CH_2O-,$$

—$SCH_2$—, —$CH_2S$—, —$NHC(R^{31})(R^{32})$—, —$NR^{37}SO_2$—,

—$SO_2NR^{27}$—, —$C(R^{31})(R^{32})NH$—, —CH=CH—,

—CF=CF—, —CH=CF—, —CF=CH—, —$CH_2CH_2$—,

-continued

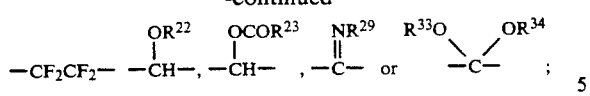

r') M is O, NM$^{19}$ or S; and s')
1. x=2 or 3,
2. y=0, 1 or 2 and
3. z=0, 1, 2, 3, 4 or 5;

and their physiologically tolerable salts.

Alkyl, alkenyl and alkynyl can be straight-chain or branched. The same applies to radicals derived therefrom, such as alkanoyl or alkoxy.

Cycloalkyl is understood is also meaning alkyl-substituted rings.

(C$_6$-C$_{12}$) is, for example, phenyl, naphthyl or biphenyl, preferably phenyl. The same applies to radicals derived therefrom, such as aroyl or aralkyl. (C$_1$-C$_9$)-Heteroaryl is in particular understood as meaning radicals which are derived from phenyl or naphthyl in which one or more CH groups are replaced by N and/or in which at least two adjacent CH groups are replaced by S, NH or O (with the formation of a five-membered aromatic ring). 1 or both atoms of the fusion site of bicyclic radicals (such as in indolizing) can furthermore also be a nitrogen atom.

These radicals are, for example, furanyl, thianyl, pyrrolyl, imidazolyl, pyrazolyl, traizolyl, tetrazolyl, oxazolyl, isoxazolyl, thiazolyl, isothiazolyl, pyridyl, prazinyl, pyrimidinyl, pridazinyl, indolyl, indazolyl, quinolyl, isoquinolyl, phthalazinyl, quinoxalinyl, quinazolinyl or cinnolinyl.

If it is assumed there that
(1) the radical R$^{14}$ is not the ortho-position and
(2) R$^{14}$ is equal to

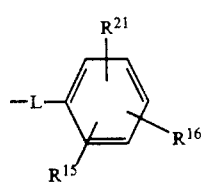

with L in the form of a single bond and R$^{21}$ is —CO$_2$H or

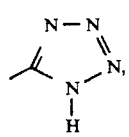

then R$^{21}$ must assume the ortho- or the meta-position; or if R$^{14}$ and L are as defined above and R$^{21}$ is N—SO$_2$CF$_3$ or —NHSO$_2$CH$_3$, then R$^{21}$ must be in the ortho-position;

(3) R$^{14}$ is

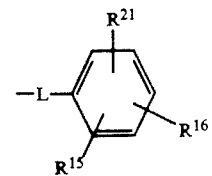

and L is not a single bond, then R$^{21}$ must be in the ortho-position, except in the case in which L is NR$^{27}$CO and R$^{21}$ is NHSO$_2$CF$_3$ or NHSO$_2$CH$_3$ and thus R$^{21}$ must be in the ortho- or meta-position;

(4) R$^{14}$ is 4—CO$_2$H or a salt derived therefrom, then the substituent in the 4-position of the imidazole ring must not be —CH$_2$OH, —CH$_2$OCOCH$_3$ or —CH$_2$CO$_2$H;

(5) R$^{14}$ is 4-CO$_2$H or a salt derived therefrom, then R$^1$ cannot be S-alkyl;

(6) R$^{14}$ is ·

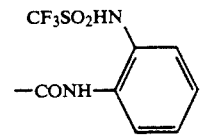

and R$^1$ is n-hexyl, then R$^2$, if Y and X are CR$^2$, is not simultaneously hydrogen;

(7) R$^1$ is not —CHF—CH$_2$CH$_2$CH$_3$ or CH$_2$OH and
(8) y=0 and R$^{14}$ is

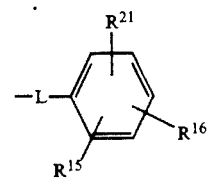

where L=—NH—CO—, R$^{21}$=2—NHSO$_2$CH$_3$ and R$^1$=n-propyl, then R$^2$, if Y and X are CR$^2$, is not —CO$_2$CH$_3$;

(9) y=0 and R$^1$ is

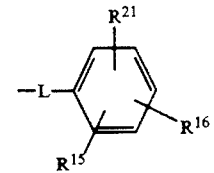

where L=—NH—CO—, R$^{21}$=2—COOH and R$^1$=n-propyl, then R$^2$, if Y and X are CR$^2$, is not —CO$_2$CH$_3$;

(10) y=1 and R$^1$ is

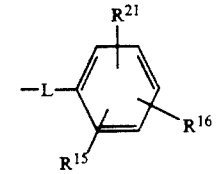

with L as a single bond and R$^2$ as —Cl or CHO, then R$^{21}$ is not 4-(tetrazol-5-yl).

Physiologically tolerable salts of compounds of the formula I are understood as meaning both their organic and inorganic salts, such as are described in Remington's Pharmaceutical Sciences, 17th edition, page 1418 (1985). On the basis of physical and chemical stability and solubility, sodium, potassium, calcium and ammonium salts, inter alia, are preferred for acidic groups; and salts with hydrochloric acid, sulfuric acid, phosphoric acid, carbonic acid or sulfonic acids, and also acetic acid, citric acid, benzoic acid, maleic acid, fumaric acid, tartaric acid and p-toluenesulfonice acid, inter alia, for basic groups.

Preferred compounds of the formula II

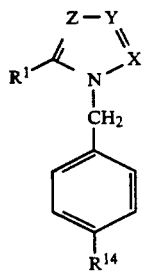
(II)

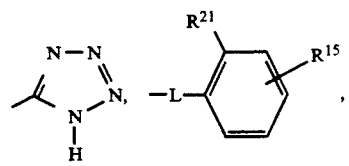

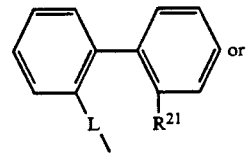

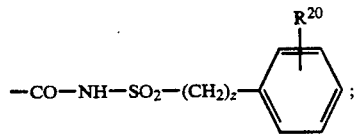

are those in which
a) X is N, Y is CH and Z is CH;
b) X is CH, Y is N and Z is CH;
c) X is CH, Y is CH and Z is N or
d) X, Y and Z are each N.

Compounds of the formula II are furthermore preferred in which
a) $R^1$ is $(C_3-C_7)$-alkyl, $(C_3-C_7)$-alkenyl or $(C_3-C_7)$-alkynyl;
b) $R^2$ is
1. chlorine,
2. bromine,
3. $C_v F_{2v+1}$ wherein $v=1, 2,$ or 3,
4. pentafluorophenyl,
5. $-S(O)_rR^6$,
6. $SF_5$,
7. $(CH_2)_{o-1}-CHR^7-OR^5$,
8. $(CH_2)_o-O-CO-R^3$,
9. $-COR^8$,
10. $-(CH_2)_o-CO-R^8$,
11. $-CH_2-NH-CO-R^8$,
12. $-(CYH_2)_o-NH-SO_2-R^9$,
13. $-CH=CH-CHR^3-OR^6$,
14. tetrazolyl$-(CH_2)_m-$,
15. $-(CH_2)_nSO_2-NH-CO-NR^6R^9$,
16. $-(CH_2)_o-SO_3R^9$ or $(C_1-C_6)$-alkyl optionally substituted by hydroxyl, preferably hydroxymethyl;
c) $R^3$ is hydrogen or $(C_1-C_4)$-alkyl;
d) $R^6$ is hydrogen, $(C_1-C_4)$-alkyl, $(C_1-C_4)$-alkanoyl or preferably $(C_2-C_9)$-heteroaryl;
e) $R^7$ is hydrogen, $(C_1-C_4)$-alkyl, $(C_1-C_9)$-heteroaryl, or $(C_6-C_{12})$-aryl-$(C_1-C_4)$-alkyl;
f) $R^8$ is hydrogen, $(C_1-C_4)$-alkyl, $OR^5$ or morpholino;
g) $R^9$ is $CF_3$, $(C_1-C_5)$-alkyl or phenyl;
h) $R^{16}$ is $-CO_2H$, $-NHSO_2CF_3$,
i) $R^{15}$ is hydrogen, $(C_1-C_4)$-alkyl, halogen or $(C_1-C_4)$-alkoxy;
j) $R^{19}$ is hydrogen or $(C_1-C_4)$-alkyl;
k) $R^{21}$ is $-CO_2H$, $-CO_2CH_2OCOC(CH_3)_3$, $NHSO_2CF_3$ and

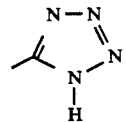

l) $R^{22}$ is hydrogen or $(C_1-C_4)$-alkyl;
m) L is a single bond, $-O-$, $-CO-$, $-NHCO-$ or $-OCH_2-$ and the other radicals and variables are as defined above.

The following four compounds are particularly preferred for their cardioprotective action:

1. 2-n-butyl-4-chloro-5-hydroxymethyl-1-[(2'-(1H-tetrazol-5-yl)biphenyl-4-yl)methyl]imidazole potassium salt, 2. 2-n-butyl-5-carboxy-4-4-chloro-1-[(2'-(1H-tetrazol-5-yl)biphenyl-4-yl)methyl]imidazole potassium salt, 3. 2-n-butyl-1-[(2'-carboxybiphenyl-4-yl)methyl]-4-chloro-5-hydroxymethylimiadzole sodium salt, 4. 2-n-butyl-5-carboxy-1-[(2'-carboxybiphenyl-4-yl)methyl]-4-chloroimidazole sodium salt.

In the practice of the method according to the invention, the antagonists of the angiotensin II receptor described above can be used on mammals such as apes, dogs, cats, rats, humans etc. The compounds suitable for the use according to the invention are expediently incorporated into pharmaceutical preparations n a customary manner. They can be brought into the customary administration forms such as capsules, tablets, coated tablets, solutions, ointments, emulsions and also into depot form. The active compound can optionally also be present in microencapsulated form. The preparations can contain physiologically tolerable organic or inorganic auxiliaries or additives, for example granulating materials, adhesives and binders, lubricants, suspending agents, solvents, antibacterial agents, wetting agents and preservatives.

The treatment according to the invention can be carried out both via the mucosa and parenterally. Oral and parenteral (such as i.v. or i.m.) administration forms are preferred.

For an oral administration form, the active compounds are mixed with the additives customary for this, such as excipients, stabilizers or inert diluents and brought into suitable administration forms, such as tablets, coated tablets, hard gelatin capsules, aqueous, alcoholic or oily suspensions or aqueous, alcohol or oily solutions, by customary methods. Inert excipients which can be used are, for example, gum arabic, magnesium carbonate, potassium phosphate, lactose, glucose or starch, in particular maize starch. Preparation in this case can be effected both as dry or moist granules. Suitable oily excipients or solvents are, for example, vegetable and animal oils, such as sunflower oil or codliver oil.

For subcutaneous or intravenous administration, the active compounds or their physiologically tolerable salts, if desired, are brought into solution, suspension or emulsion with the substances customary for this, such as solubilizers, emulsifiers or other auxiliaries. Suitable solvents for the active combinations and the corresponding physiologically tolerable salts are, for example: water, physiological saline solutions or alcohols, for example ethanol, propanediol or glycerol, and in addition also sugar solutions such as glucose or mannitol solutions or alternatively a mixture of the various solvents mentioned.

The compounds of the formula I are preferably administered in doses of 0.1 to 100 mg/kg, in particular preferably 0.1 to 50 mg, in particular 1 to 30 mg, being given once to three times daily.

Test

Action of the angiotensin II receptor antagonist 2-n-butyl-4-chloro-5-hydroxymethyl-1-[(2'-(1H-tetrazol-5-yl)biphenyl-4-yl)methyl]imidazole potassium salt (compound 1) on development and regression of cardiac hypertrophy in rats

Method

Cardiac hypertrophy was induced in conscious rats by constriction of the abdominal aorta. After hypertrophy was fully established, groups of the animals received 3mg/kg of the compound 1 administered via their drinking water for 6 weeks. In the prevention experiment, the administration of the antagonist began immediately. In the regression experiment, on the other hand, it did not begin until 6 weeks after setting up the aortic stenosis. Control groups without administration of substance (CON) and sham-operated animals (SHAM) were additionally used. At the end of the observation period, the animals were sacrificed and the heart weight, the wall thickness in the left ventricle and the myocardial protein content were determined.

The significant changes in the $\delta HW\%$ value of 24% and 17% shown in this table confirm the preventive and regressive action of the compound 1 in relation to cardiac hypertrophy.

The following examples indicate the administration forms for the treatment of cardiac and of vascular hypertrophy and hyperplasia by the method according to the invention. The compounds of the formula I and formula II can be brought into the corresponding administration forms analogously to the examples.

EXAMPLE 1

Preparation of the agent used according to the invention for oral administration in the treatment of cardiac and of vascular hypertrophy and hyperplasia.

1,000 tablets, which each contain 20 mg of 2-n-butyl-4-chloro-5-hydroxymethyl-1-[(2'-(1H-tetrazol-5-yl)biphenyl-4-yl)-methyl]imidazole potassium salt, are prepared using the following auxiliaries:

| | |
|---|---|
| 2-n-butyl-4-chloro-5-hydroxymethyl-1-[(2'-(1H-tetrazol-5-yl)biphenyl-4-yl)methyl]imidazole potassium salt | 20.0 g |
| maize starch | 140.0 g |
| gelatin | 7.5 g |
| microcrystalline cellulose | 2.5 g |
| magnesium stearate | 2.5 g |

2-n-Butyl-4-chloro-5-hydroxymethyl-1-[(2'-(1H-tetrazol-5-yl)biphenyl-4-yl)methyl]imidazole potassium salt and maize starch are mixed with an aqueous gelatin solution. The mixture is dried and ground to give granules. Microcrystalline cellulose and magnesium stearate are mixed with the granules. The resulting granules are compressed to give 1,000 tablets, each tablet containing 20 mg of the angiotensin II receptor antagonist. These tablets can be used for the treatment of cardiac and of vascular hypertrophy and hyperplasia.

EXAMPLE 2

Analogously to Example 1, 1,000 tablets are prepared which each contain 3 mg of 2-n-butyl-4-chloro-5-hydroxymethyl-1-[(2'-(1H-tetrazol-5-yl)biphenyl-4-yl)methyl]imidazole potassium salt by using 3 g of this compound in the formulation described in Example 1.

EXAMPLE 3

Gelatin capsules, which each contain 20 mg of 2-n-butyl-4-chloro-5-hydroxymethyl-1-[(2'-(1H-tetrazol-5-yl)biphenyl-4-yl)methyl]imidazole potassium salt, are filled with the following mixture:

| | |
|---|---|
| 2-n-butyl-4-chloro-5-hydroxymethyl-1-[(2'-(1H-tetrazol-5-yl)biphenyl-4-yl)methyl]-imidazole | 20 g |

| | Test result | | | | | |
|---|---|---|---|---|---|---|
| | PREVENTION (n: 17) | | | REGRESSION (n: 18) | | |
| | SHAM | CON | 1 | SHAM | CON | 1 |
| MAB | 92 ± 2* | 153 ± 4# | 118 ± 3#* | 97 ± 3* | 134 ± 4 | 111 ± 3#* |
| HW | 316 ± 9* | 426 ± 15# | 392 ± 10#* | 303 ± 10* | 398 ± 11# | 353 ± 15#* |
| δHW % | — | +35%# | +24%#* | — | +31%# | +17%#* |

$p < 0.05 =$ * = against control group;
\# = against sham control;
HW = heart weight (mg/100 g of body weight);
MAB = mean arterial blood pressure (mm Hg)

| -continued | |
|---|---|
| potassium salt | |
| potassium stearate | 1 mg |
| lactose | 214 mg |

These capsules can be used for the treatment of cardiac and of vascular hypertrophy and hyperplasia.

EXAMPLE 4

Analogously to Example 3, using 3 g of active compound, gelatin capsules are prepared which each contain 3 mg of 2-n-butyl-4-chloro-5-hydroxymethyl-1-[(2'-(1H-tetrazol-5-yl)biphenyl-4-yl)methyl]imidazole potassium salt.

EXAMPLE 5

The preparation of an injection solution for the treatment of cardiac and of vascular hypertrophy and hyperplasia is described below:

| | |
|---|---|
| 2-n-butyl-4-chloro-5-hydroxymethyl-1-[(2'-(1H-tetrazol-5-yl)biphenyl-4-yl)methyl]-imidazole potassium salt | 1 g |
| methylparaben | 5 g |
| propylparaben | 1 g |
| sodium chloride | 25 g |
| water for injection | 5 l |

2-n-Butyl-4-chloro-5-hydroxymethyl-1-[(2'-(1H-tetrazol-5-yl)biphenyl-4-yl)methyl]imidazole potassium salt, the preservatives and sodium chloride are dissolved in 3 l of water for injection and the solution is made up to 5 l with water for injection. The solution is sterile filtered and aseptically filled into presterilized bottles which are sealed with sterilized rubber caps. Each bottle contains 5 ml of solution.

EXAMPLE 6

Tablets which can be used for the treatment of cardiac and of vascular hypertrophy and hyperplasia are prepared as described in Example 1, except that, instead of 2-n-butyl-4-chloro-5-hydroxymethyl-1-[(2'-(1H-tetrazol-5-yl)biphenyl-4-yl)methyl]imidazole potassium salt, 2-n-butyl-5-carboxy-4-chloro-1-(1H-tetrazol-5-yl)biphenyl-4-yl)methyl]imidazole potassium salt or 2-n-butyl-1-[(2'-carboxybiphenyl-4-yl)-methyl]-4-chloro-5-hydroxymethyl-imidazole potassium salt, 2-n-butyl-5-carboxy-1-[(2'-carboxybipheny-4-yl)-methyl]-4-chloroimidazole potassium salt or the corresponding sodium salts are used.

EXAMPLE 7

An injection solution is prepared analogously to the procedure described in Example 5, except that, instead of 2-n-butyl-4-chloro-5-hydroxymethyl-1-[(2'-(1H-tetrazol-5-yl)biphenyl-4-yl)methyl]imidazole potassium salt, 2-n-butyl-5-carboxy-4-chloro-1-[(2'-(1H-tetrazol-5-yl)biphenyl-4-yl)methyl]imidazole potassium salt or 2-n-butyl-1-[(2'-carboxybiphenyl-4-yl)methyl]-4-chloro-5-hydroxymethylimidazole potassium salt, 2-n-butyl-5-carboxy-1-[(2'-carboxybiphenyl-4-yl)-methyl]-4-chloroimidazole potassium salt or the corresponding sodium salts are used.

We claim:

1. A method for the treatment of cardiac hypertrophy or hyperplasia comprising the step of administering to a mammal in need thereof an effective amount of a compound of formula II

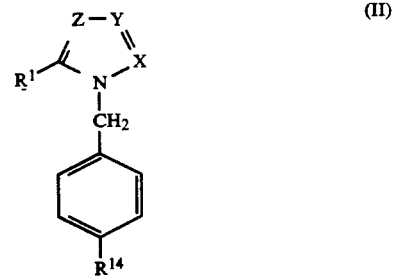

or a physiologically salt thereof, wherein:
X, Y are identical or different and are $CR^2$;
Z denotes N;
$R^1$ is $(C_3-C_7)$-alkyl, $(C_3-C_7)$-alkenyl or $(C_3-C_7)$-alkynyl;
$R^2$ is chlorine; bromine; $C_vF_{2v+1}$, where $v=1$, 2 or 3; pentafluorophenyl; $-S(O)_rR^6$, where r is 0, 1 or 2; $SF_5$; $(CH_2)_{o-1}-CHR^7-OR^5$; $(CH_2)_o-O-CO-R^3$; $-COR^8$; $-(CH_2)_o-CO-R^8$, $-CH_2-NH-CO-R^8$; $-(CH_2)_o-NH-SO_2-R^9$; $-CH=CH-CHR^3-OR^6$; tetrazoyl$-(CH_2)_m-$, where m is an integer from 0 to 5; $-(CH_2)_nSO_2-NH-CO-NR^6R^9$, where n is an integer from 1 to 5; $-(CH_2)_o-SO_3R^9$ or $(C_1-C_6)$-alkyl optionally substituted by hydroxyl; and o is an integer from 1 to 10;
$R^3$ is hydrogen or $(C_1-C_4)$-alkyl;
$R^5$ is hydrogen, $(C_1-C_4)$-alkyl, phenyl or benzyl;
$R^6$ is hydrogen, $(C_1-C_4)$-alkyl, $(C_1-C_4)$-alkanoyl or $(C_2-C_9)$-heteroaryl;
$R^7$ is hydrogen, $(C_1-C_4)$-alkyl, $(C_1-C_9)$-heteroaryl, or $(C_6-C_{12})$-aryl-$(C_1-C_4)$-alkyl;
$R^8$ is hydrogen, $(C_1-C_4)$-alkyl, $OR^5$ or morpholino;
$R^9$ is $CF_3$, $(C_1-C_6)$-alkyl or phenyl;
$R^{14}$ is $-CO_2H$, $-NHSO_2CF_3$,

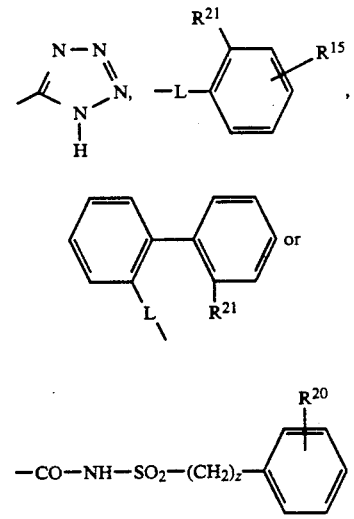

wherein $z=0$, 1, 2, 3, 4 or 5;
$R^{15}$ is hydrogen, $(C_1-C_4)$-alkyl, halogen or $(C_1-C_4)$-alkoxy;
$R^{19}$ is hydrogen or $(C_1-C_4)$-alkyl;
$R^{20}$ is hydrogen, methyl or benzyl;

$R^{21}$ is —$CO_2H$, —$CO_2CH_2OCOC(CH_3)_3$, $NHSO_2CF_3$ or

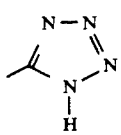

$R^{22}$ is hydrogen or ($C_1$–$C_4$)-alkyl; and

L is a single bond, —O—, —CO—, —NHCO— or —$OCH_2$—.

2. The method of claim 1 wherein said compound of formula II is the potassium salt of 2-n-butyl-4-chloro-5-hydroxymethyl-1-[(2'-(1H-tetrazol-5-yl)biphenyl-4-yl)methyl]imidazole.

3. The method of claim 1 wherein said compound of formula II is the potassium salt of 2-n-butyl-5-carboxy-4-chloro-[(2'-(1H-tetrazol-5-yl)-biphenyl-4-yl)methyl]imidazole.

4. The method of claim 1 wherein said compound of formula II is the sodium salt of 2-n-butyl-1-[(2'-carboxybiphenyl-4-yl)-methyl]-4-chloro-5-hydroxymethylimidazole.

5. The method of claim 1 wherein said compound of formula II is the sodium salt of 2-n-butyl-5-carboxy-1-[(2'-carboxybiphenyl-4-yl)-methyl]-4-chloroimidazole.

* * * * *